(12) United States Patent
Rehman et al.

(10) Patent No.: US 10,386,352 B2
(45) Date of Patent: *Aug. 20, 2019

(54) POWER TRANSFORMER COPPER SULFIDE MONITORING SYSTEM

(71) Applicant: King Fahd University of Petroleum and Minerals, Dhahran (SA)

(72) Inventors: Shafiqur Rehman, Dhahran (SA); Luai M. Alhems, Dhahran (SA); Ramsey Jadim, Vaxjo (SE)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 15/971,760

(22) Filed: May 4, 2018

(65) Prior Publication Data

US 2018/0275107 A1 Sep. 27, 2018

Related U.S. Application Data

(63) Continuation of application No. 14/857,332, filed on Sep. 17, 2015, now Pat. No. 9,983,188.

(51) Int. Cl.
*G01N 33/28* (2006.01)
*G01N 33/00* (2006.01)
*G01K 13/00* (2006.01)

(52) U.S. Cl.
CPC ......... *G01N 33/0044* (2013.01); *G01K 13/00* (2013.01); *G01N 33/287* (2013.01)

(58) Field of Classification Search
CPC .............................. G01R 31/16; G01N 33/287
See application file for complete search history.

(56) References Cited

U.S. PATENT DOCUMENTS 8,854,053 B2    10/2014  Hosokawa

FOREIGN PATENT DOCUMENTS

CN    104133165 A    11/2014
JP    57-40652       3/1982
(Continued)

OTHER PUBLICATIONS

Sundara et al (Influence of Metal Passivator on the Corrosion of Copper Conductors due to Sulphur in Oil, Proceedings of 2008 International Symposium on Electrical Insulating Materials, Sep. 7-11, 2008).

(Continued)

*Primary Examiner* — Clayton E. LaBalle
*Assistant Examiner* — Leon W Rhodes, Jr.
(74) *Attorney, Agent, or Firm* — Oblon, McClelland, Maier & Neustadt, L.L.P.

(57) ABSTRACT

An apparatus for measuring the rate of $Cu_2S$ formation in power transformers comprising a sealable transformer vessel and a sealable lid with at least four sealable ports, and an internal apparatus configuration involving a copper metal sheet, a power transformer, a temperature sensor, and a weighing device providing real-time feedback data, whereby these components are submerged in an effective amount of a reactive sulfur-containing transformer oil and sealed. An inert gas atmosphere is provided within the transformer vessel by a gas bubbler. The transformer oil is heated with a heating bath to a reactive temperature for $Cu_2S$ production. A method of measuring the rate of $Cu_2S$ formation whereby the apparatus is purged with an inert gas, heated to a reactive temperature, examined for $Cu_2S$ formation, the $Cu_2S$ produced is quantified and the rate of formation of $Cu_2S$ is calculated.

8 Claims, 6 Drawing Sheets

(56) References Cited

FOREIGN PATENT DOCUMENTS

| JP | 2000353623 A | 12/2000 |
|---|---|---|
| JP | 2003289008 A | 10/2003 |
| JP | 2000353623 A | 4/2009 |
| JP | 2010-27634 | 2/2010 |
| WO | WO 2009054156 A1 | 4/2009 |

OTHER PUBLICATIONS

Kawarai et al (Role of Dissolved Copper and Oxygen on Copper Sulfide Generation in Insulating Oil, IEEE Transactions on Dielectrics and Electrical Insulation vol. 16, No. 5; Oct. 2009).

Pradhan et al (Diagnostic Testing of Oil-impregnated Paper Insulation in Pro-rated Power Transformers under Accelerated Stress, Conference Record of the 2004 IEEE International Symposium on Electrical Insulation, Indianapolis Sep. 19-22, 2004).

POWER TRANSFORMER COPPER SULFIDE MONITORING SYSTEM

CROSS-REFERENCE TO RELATED APPLICATION

The present application is a Continuation of Ser. No. 14/857,332, pending, having a filing date of Sep. 17, 2015.

STATEMENT OF ACKNOWLEDGEMENT

This project was funded by King Fand University of Petroleum & Minerals and King Abdul-Aziz City of Science and Technology under project number.

BACKGROUND OF THE INVENTION

Technical Field

The present invention relates to a device and method for measuring the rate of formation of corrosive sulfur species in power transformers.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Internal corrosion damage from reactive sulfur containing components is a common problem for power transformers. Reactive sulfur species form $Cu_2S$ sulfide by reacting with a transformer's copper windings and copper surfaces. $Cu_2S$ formation on copper surfaces results in the formation of partial discharges, reduced dielectric resistance of insulating materials, arcing between conductive surfaces and ultimately electrical explosions [See Wilson, A. C. M., 1980, "Insulating Liquids: Their Uses, Manufacture and Properties," *IEEE* incorporated herein by reference in its entirety]. The prolonged exposure of sulfur containing components to elevated temperatures within the transformer induces the release of reactive species [See Peterchuck, D., Pahwa, A., 2002, "Sensitivity of transformer's hottest-spot and equivalent aging to selected parameters," *Power Delivery, IEEE Transactions on*, October, 17, (4), pp. 996-1001 incorporated herein by reference in its entirety].

The rate of $Cu_2S$ formation within power transformers is dependent upon the type of reactive sulfur species present, the time the metal surface is exposed to the reactive sulfide source, and the temperature at which the exposure takes place [See Amimoto, T., 2009, "Identification of Affecting factors of copper sulfide deposition on insulating paper in oil," *IEEE Transactions Dielectric. Electr. Insul.*, 16, (4), pp. 265-272 incorporated herein by reference in its entirety]. A number of apparatuses exist to determine the rate of $Cu_2S$ formation within power transformers. The immersion of copper strips and windings in sealed vessels with a variety of reactive sulfur containing transformer oils, [See, Hosokawa, U.S. Pat. No. 8,854,053B2, incorporated herein by reference in its entirety], allows investigators to analyze the transformer oils contribution to $Cu_2S$ formation. The addition of model power transformers allows for increasingly more in-depth analyses of transformer oil properties within transformer systems.

Despite the known contribution of corrosives species from transformer oils, the contribution from non-oil sulfur containing components to the rate of $Cu_2S$ formation is mistakenly ignored. The dielectric paper used to insulate conductive metal surfaces within the transformer is composed of up to 41% sulfur [See Lewand, L. R. 2002, "The role of corrosive sulfur in transformers and transformer oil." In Proceedings of the Sixty-Ninth Annual International Conference of Doble Clients, incorporated herein by reference in its entirety]. Additionally, transformer gaskets which are in direct contact with metal surfaces contain up to 55% sulfur [See Lewand, L. R. 2002, "The role of corrosive sulfur in transformers and transformer oil." In Proceedings of the Sixty-Ninth Annual International Conference of Doble Clients, incorporated herein by reference in its entirety]. Subsequently, the rate of $Cu_2S$ formation within a power transformer system is an aggregate of the contributions of multiple sulfur containing sources and competitive metal sulfide reactions. Current immersion tank methods and apparatuses tabulate the rate of $Cu_2S$ formation without distinguishing the contributions of multiple reactive sulfur containing sources.

The presence of competitive degradative sulfur reactions on other transformer surfaces also skews $Cu_2S$ formation rates. The iron core found in liquid Iron core transformers, and iron/steel transformer vessels walls, are both chemically altered by reactive sulfur species at elevated temperatures [See N'cho, J. S., Fofana, I., Beroual, A., Ngnui, A. T. 2015, "Parameters affecting the formation of corrosive sulphide deposition on copper conductors," $17^{th}$ International Symposium on High Voltage Engineering, April—incorporated herein by reference in its entirety]. Drawing reactive sulfur away from copper sulfide formation to the iron sulfide formation pathway lowers the total amount of copper sulfide and truncates its rate of formation value.

The gaseous environment within a power transformer can effect the rate of $Cu_2S$ formation as well. For example, free breathing transformers (i.e. transformers which are at least partially open to the atmosphere) operate at >100 ppm oxygen levels [See, Bengtsson, C. et al., 2006, "Oil Corrosion and Coducting $Cu_2S$ Deposition in Power Transformer Windings," Cigre—incorporated herein by reference in its entirety]. High levels of oxygen (>100 ppm) within a transformer promotes a breakdown of dielectric insulation paper, resulting in greater amounts of dissolved sulfur products including copper sulfate. Conversely, low oxygen levels (found in sealed transformer apparatus) promote anaerobic $Cu_2S$ formation leading to superficially enlarged rates of formation [See Melchiore, J. J. 1967, "Factors Affecting Stability of Transformer and Cable Oils" In Proceedings of the Seventh Electrical Insulation Conference, *IEEE*, October, incorporated herein by reference in its entirety]. At elevated temperatures the previously mentioned process is accelerated [See Ryder, S. 2009, "Transformer Design and Sulphur Corrosion: The Missing Link" In Proceedings of the Seventy-Sixth Annual International Conference of Doble Clients, incorporated herein by reference in its entirety], while gaseous by-products are produced [See Papadopoulos, A., Psomopoulos, C. S., 2014, "Dissolved Gas Analysis for the evaluation of the Corrosive Sulphur activity in Oil Insulated Power Transformers." November, Proceedings IET Medpower—incorporated herein by reference in its entirety]. Single directional gas flow mechanisms that do not possess dynamic methods for correcting and recovering gaseous environments alter the copper sulfide reaction pathway and skew rate determination results.

Standard material characterization and analysis involves removing $Cu_2S$ from the vessel. However, $Cu_2S$ readily forms $CuSO_4$ and $Cu_2SO_4$ in oxygen rich environments. This conversion results in a significant mass difference with weighed $Cu_2S$. Additionally dissolved metals begin to form oxides and precipitate in air, while high temperature reactions require a cooling period before extraction allowing for metal oxide and metal sulfate formation to occur.

In view of the forgoing, the objective of the present disclosure is to provide a device and method for measuring the rate of formation of corrosive sulfur species in power transformers.

BRIEF SUMMARY OF THE INVENTION

According to a first aspect, the present disclosure relates to an apparatus, including i) a transformer vessel with a sealable lid comprising at least four sealable ports, and a flange on both the vessel and the sealable lid ii) a copper metal sheet held in the vessel with a first holder connected to a first sealable port iii) a power transformer comprising iron strips and copper windings coated with an insulating dielectric paper, wherein the power transformer is held in the vessel with a second holder connected to a second sealable port iv) a temperature sensor held in the vessel with a third holder connected to a second sealable port v) a gas bubbler fluidly connected to a fourth sealable port and an inert gas source, where the gas bubbler maintains an inert atmosphere and constant pressure within the transformer vessel vi) a heating bath that heats the transformer vessel and vii) a reactive sulfur-containing insulating transformer oil that submerges the held copper metal sheet, the power transformer, and the temperature sensor. The apparatus of the present disclosure isolates reactive sulfur species from the reactive sulfur containing insulating transformer oil to determine a rate of $Cu_2S$ deposit formation.

In one embodiment, the transformer vessel further includes a gasket seated on the flange of the vessel, and when sealed, the gasket is sandwiched between the flange of the transformer vessel and the flange of the sealable lid.

In one embodiment, the sealable lid is secured to the transformer vessel via at least one fastener selected from the group consisting of a clamp, a screw, a bolt, and an adhesive by fastening together the flange of the transformer vessel and the sealable lid flange.

In one embodiment, the transformer vessel and the sealable lid are transparent.

In one embodiment, the transformer vessel and the sealable lid comprise glass.

In one embodiment, the temperature sensor is a thermocouple having more the one metallic alloy and a conductive wire.

In one embodiment, the apparatus further includes a heating source temperature controller that is electrically connected to the heating source, the thermocouple, and a display, where the conductive wire of the thermocouple links the metallic alloys to the heating bath temperature controller.

In one embodiment, the thermocouple provides internal transformer temperature feedback data to the heating bath temperature controller.

In one embodiment, the insulating dielectric paper comprises cellulose.

In one embodiment, the reactive sulfur containing insulating transformer oil comprises at least one reactive sulfur containing species selected from the group consisting of elemental sulfur and thiol.

In one embodiment, the apparatus of the present disclosure further includes a weighing device attached to the first holder for measuring the mass/weight of $Cu_2S$ formed on the copper metal sheet.

According to a second aspect, the present disclosure relates to a method for measuring reactive sulfur species formation in a power transformer, involving i) purging an apparatus with an inert gas ii) heating the apparatus to a reactive temperature with the heating bath iii) removing the $Cu_2S$ deposited copper metal sheet and the power transformer from the apparatus iv) examining the copper metal sheet, the insulating dielectric paper and the power transformer for $Cu_2S$ deposits v) quantifying the $Cu_2S$ deposits to determine the levels of reactive sulfur species formation present in the reactive sulfur containing insulating transformer oil and vi) calculating the rate of $Cu_2S$ deposits formation.

In one embodiment, the reactive temperature is 40-120° C.

In one embodiment, the heating is carried out for up to 30 days.

In one embodiment, the internal vessel temperature is measured by the temperature sensor.

In one embodiment, the examining is conducted through the transparent transformer vessel and/or the transparent sealable lid.

In one embodiment, examining the $Cu_2S$ comprises using at least one characterization method selected from the group consisting of XRD, SEM, and ICP.

In one embodiment, quantifying the $Cu_2S$ deposits comprises using an initial mass of the copper sheet subtracted from a final mass of the copper sheet.

In one embodiment, the calculating comprises plotting the mass of $Cu_2S$ formed at a reactive temperature as function of time of formation.

In one embodiment, the calculating further comprises fitting the mass of $Cu_2S$ vs time of formation data to a model and calculating the rate of formation.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
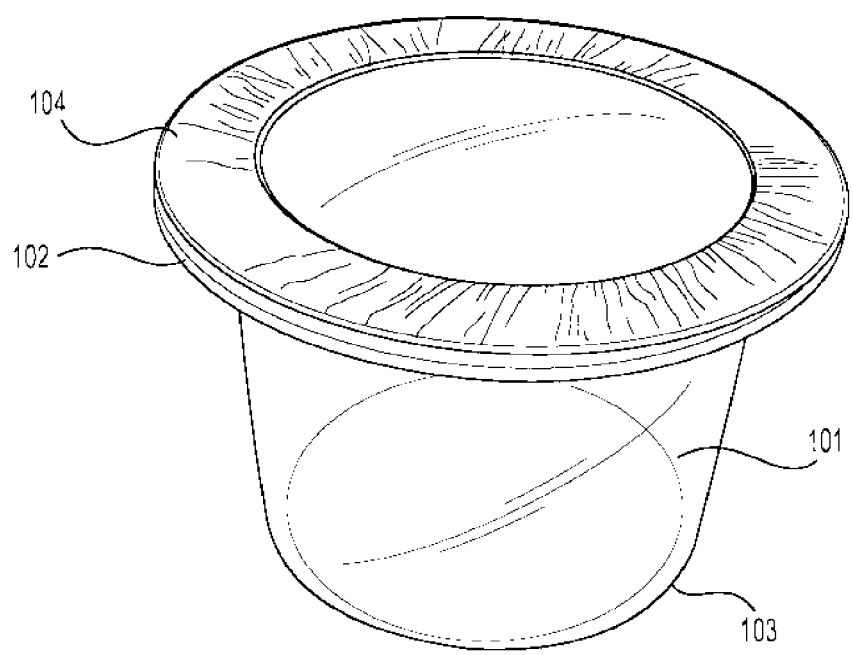
FIG. 1 is an illustration of a flanged transformer vessel with O-ring gasket.
Figure 2:
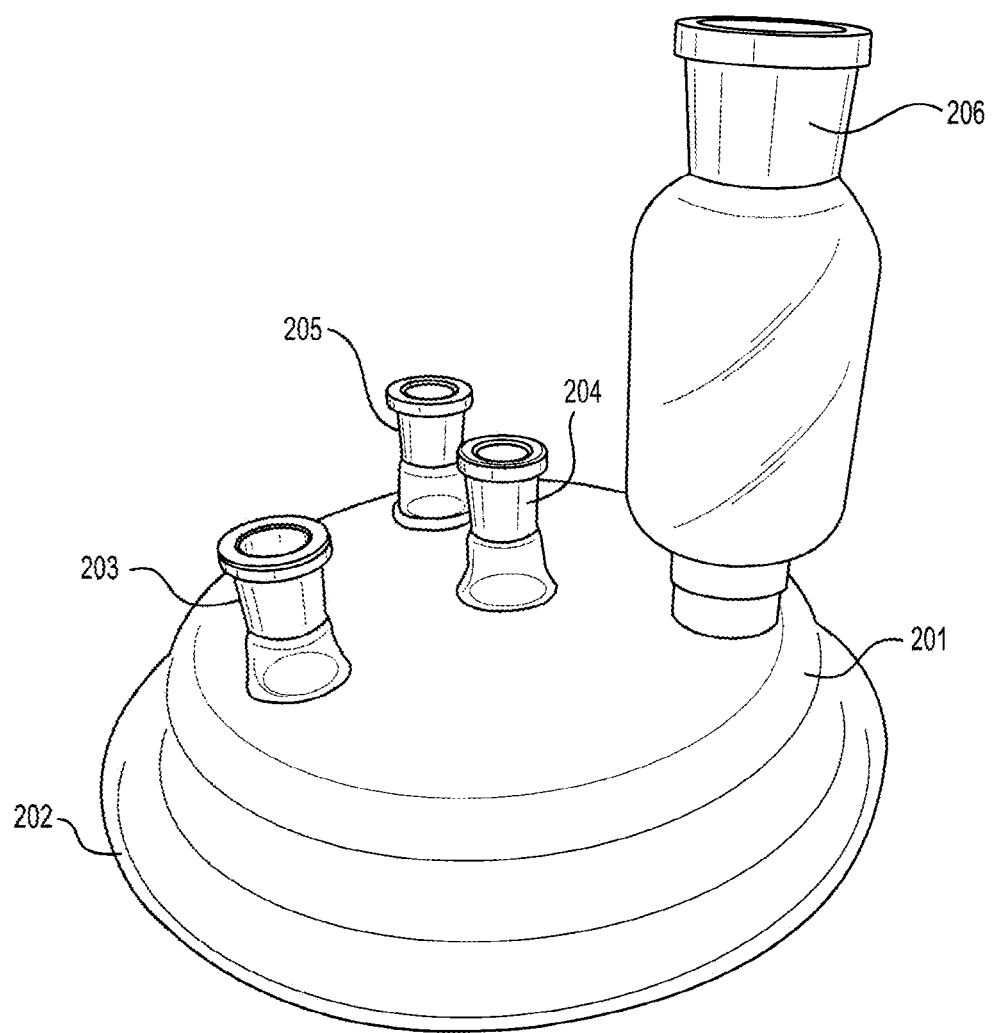
FIG. 2 is an illustration of a flanged sealable lid with sealable ports.
Figure 3:
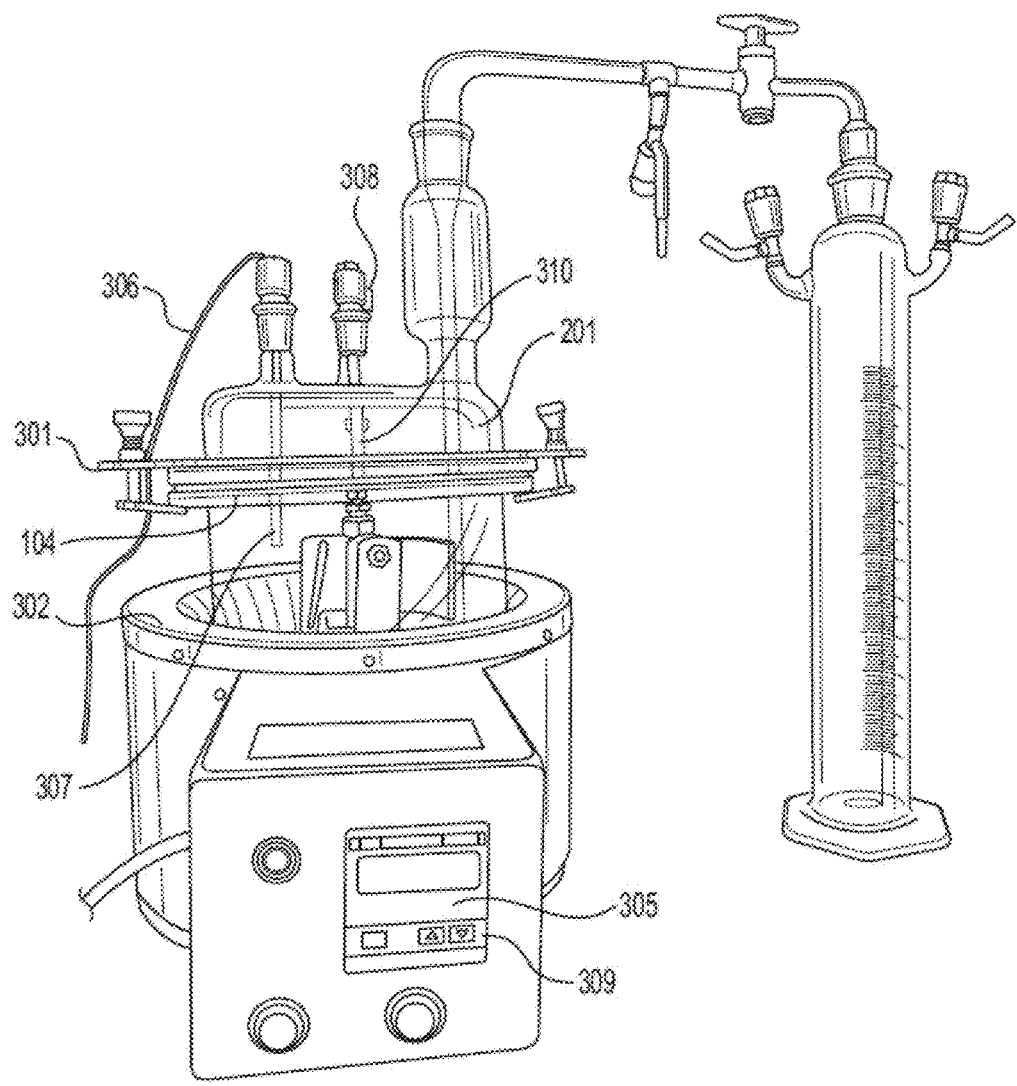
FIG. 3 is an illustration of a complete experimental setup assembly.
Figure 4:
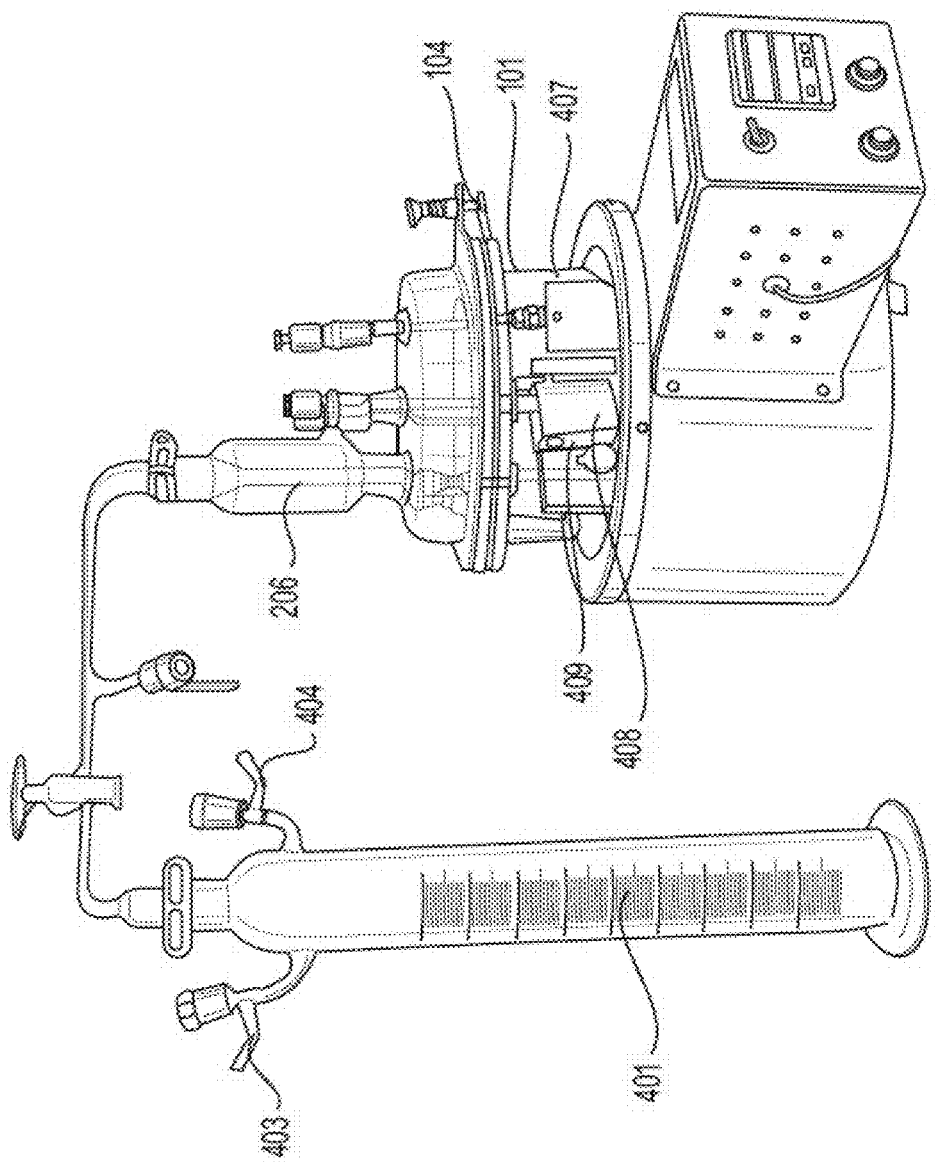
FIG. 4 is another view illustration of the complete experimental setup assembly.
Figure 5:
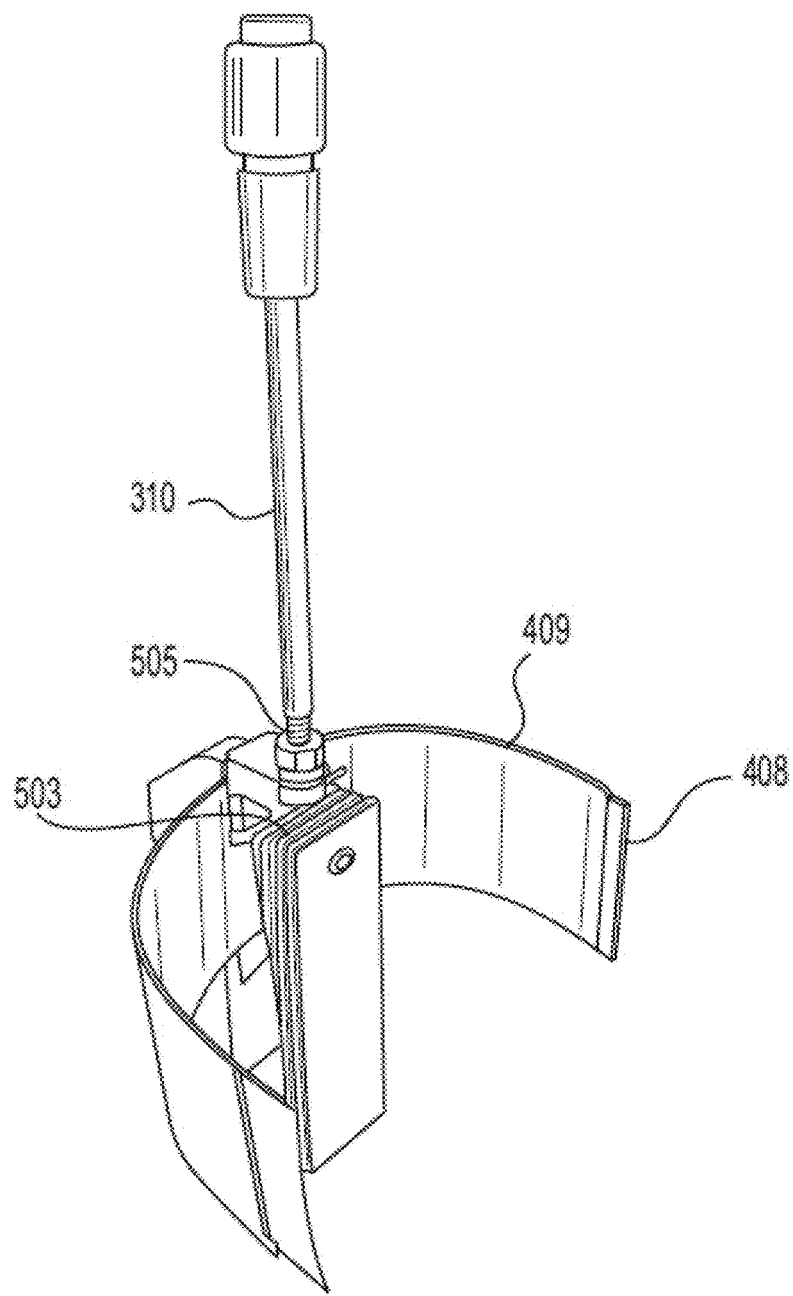
FIG. 5 is an illustration of a complete copper winding and power transformer holder assembly.
Figure 6:
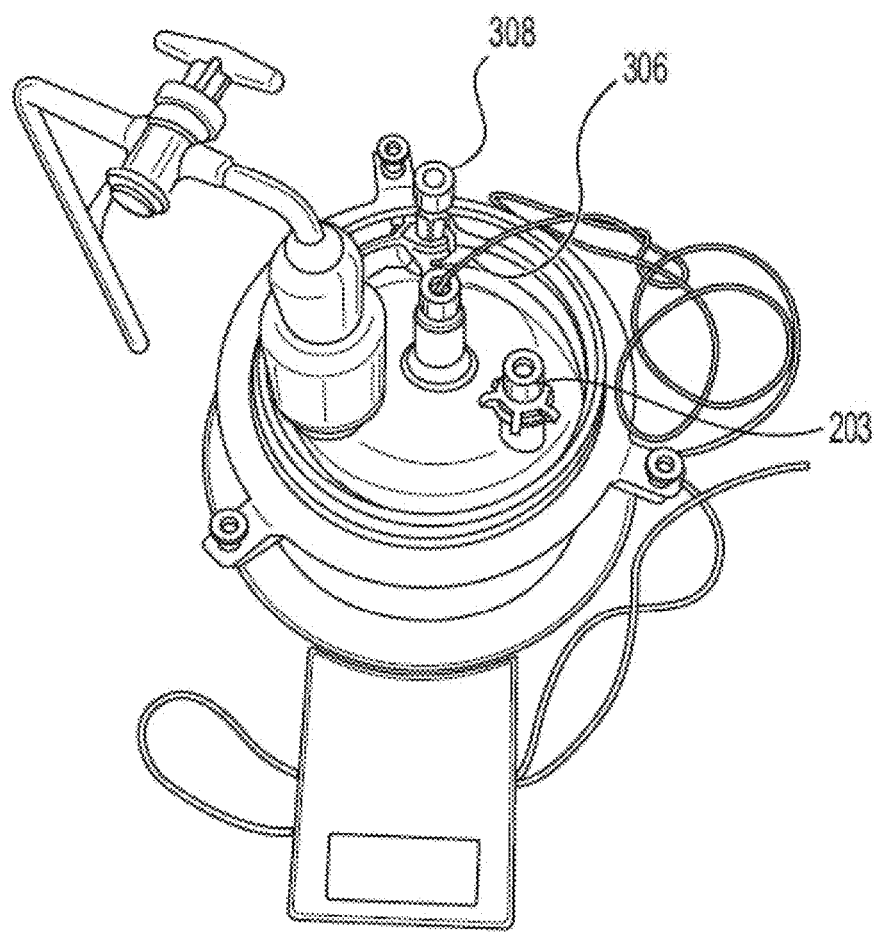
FIG. 6 is a top view illustration of the transformer vessel and sealable lid assembly in a heating bath.

Referring now to the drawings, wherein like reference numerals designate identical or corresponding parts throughout the several views.

Electrical transformer system components such as transformer oils, gaskets and dielectric papers serve as insulative mediums. Corrosive sulfur species originating from these components can degrade active metal surfaces resulting in the formation of metal sulfides such as $Cu_2S$. Subsequently, the rate of $Cu_2S$ formation from sulfur containing components needs to be determined to avoid transformer device failures stemming from metal deterioration. Additionally, $Cu_2S$ formation tends to be oxygen sensitive and requires an oxygen free atmosphere to be tested accurately. Therefore, a device is required to determine the rate of formation of $Cu_2S$ deposits.

According to a first aspect, the present disclosure relates to an apparatus for determining the rate of formation of $Cu_2S$ deposits due to sulfur containing transformer components. The apparatus may include a transformer vessel with a sealable lid comprising at least four sealable ports, as well as a flange on both the vessel and the sealable lid.

In the present disclosure, the transformer vessel (101) may be a container of any shape (e.g. cup-shaped, spherical, cylindrical, cubical, etc.) or material provided it can hold an effective amount of a reactive sulfur containing insulating transformer oil, includes a flanged open end (102), an unflanged closed end (103) and allows viewing of the internal vessel environment. In one embodiment, the transformer vessel is a flanged hollow cylinder.

The transformer vessel flange could be a continuous extension of the transformer vessel's structure. In one embodiment, the transformer vessel and the transformer vessel's flange are formed together as a single continuous flanged cylinder. It can also be envisioned where the transformer vessel and the transformer vessel's flange are separate components. The transformer vessel's flange could be oriented along several vectors relative to the ground. In one embodiment, the transformer vessel's flange is flat extending outwardly, and parallel to the ground. The transformer vessel's flange could also be envisioned in an angular orientation relative to the ground (i.e. not parallel and not perpendicular to the ground).

In the present disclosure, the sealable lid (201) could be in any shape provided there is a flanged portion of the lid (202) capable of completely and congruently overlaying the transformer vessel's open flanged end (102) and forming a seal between them. It could be advantageous for the sealable lid and the transformer vessel to have similar shapes to provide a connection with a strong seal. In one embodiment, the sealable lid is cubic with a square flange wherein the transformer vessel is also a cubic shape with a square flange. In one embodiment the sealable lid (202) is a cylinder with a circular flange wherein the transformer vessel is also a cylinder with a circular flange.

In the present disclosure, the sealable lid also has a plurality of ports of any shape or material, provided the ports are of a sufficient size to securely accommodate holders of varying sizes attached to internal transformer vessel components, while maintaining the integrity of the internal vessel environment (i.e. the ports also form a seal and do not allow gas to ingress or egress). The sealable lid may have at least two ports, preferably at least three ports, more preferably at least four ports. In one embodiment, the sealable lid has four ports (203/204/205/206). In one embodiment the ports are positioned on top of the sealable lid extending upward and perpendicular to the ground surface wherein the sealable ports are made of ground glass with teflon screw valves. However, the ports could be envisioned anywhere on the transformer vessel or the sealable lid. For instance, in one embodiment, the $1^{st}$, $2^{nd}$ and $3^{rd}$ and sealable ports are spaced equally around the circumference of a cylindrical transformer vessel extending outwardly parallel to the ground surface.

In the present disclosure, the transformer vessel, sealable lid and flanges could be made of the same transparent material. In one embodiment the transformer vessel, flanges and sealable lid are made of ground glass. The transformer vessel, flanges and sealable lid could be envisioned to be made of materials other than glass. In one embodiment, the transformer vessel, sealable lid and flanges are made of a transparent polymer. Exemplary transparent polymers include polyethylene, and polyvinylchloride. It can also be envisioned where the sealable lid, flanges and the transformer vessel are not transparent. In one embodiment, both the lid and the vessel are an opaque plastic and an optical device provides feedback data on the vessel's internal environment.

An optical device as used herein refers to any apparatus that allows visual information about the internal vessel environment to be collected from outside the environment without disrupting or altering the internal conditions. Exemplary optical devices include a sealed transparent aperture or window on the transformer vessel or an elongated fiber optic camera passed through a sealable port. In one embodiment the fiber optic camera is connected to an externally mounted eyepiece and a handle for gripping and manipulating the position of the camera's viewing area. In one embodiment a fiber optic camera is passed through a sealable connected to an externally mounted computer, wherein the camera viewing and camera positioning are manipulated through computer centered drivers.

In the present disclosure, the transformer vessel's flanged open end involves combining with a flanged sealable lid (201) to form a seal.

A "seal" as used herein refers to a tight uniform non permeable barrier between the inside and outside environments of the vessel. The seal is held by at least one fastener (301). A "fastener" as used herein will refer to a clamp, a screw, a bolt, and/or an adhesive, used to bind two or more separate items together to form a non-permeable seal. In one embodiment, the sealable lid is secured to the transformer vessel via a clamp by fastening together the flange of the transformer vessel and the sealable lid flange. In one embodiment, the seal further involves a gasket (104) sandwiched between the flange of the transformer vessel and the flange of the sealable lid. A gasket (104) may provide an additional barrier for the internal vessel environment, while also providing a better fit between the two flanged surfaces. In one embodiment the gasket is an O-ring composed of rubber and seated around the transformer vessel's flange. Exemplary gasket materials include acrylonitrile-butadiene copolymers (e.g. BUNA-N®) and fluoropolymer elastomers (e.g. Viton®).

An "effective amount" refers to a volume of liquid that submerges or at least partially submerges the internal active components of the apparatus in order to perform the prescribed function without overflowing the vessel confines when all internal components are in place. In one embodiment, at least 30%, at least 40%, at least 50%, at least 60%, at least 70% of a transformer vessel's internal volume is filled with transformer oil. Alternate effective amounts can be envisioned based upon the liquid displacement due to variances in the size of internal components and the transformer vessel.

The present disclosure also relates to an apparatus incorporating a copper metal sheet (407) held in the vessel with a first holder (307) connected to a first sealable port (203).

The copper metal sheet provides a reaction surface where the $Cu_2S$ may form. However, other metals with active binding to "chalcogenides" such as, sulfur, selenium and tellurium could be used. Exemplary alternative metals include, but are not limited to zinc, aluminum, silver, nickel, iron, cobalt, manganese, chromium, titanium, vanadium, lanthanides, actinides and cadmium. Additionally, the metal sheets length, width, thickness and morphology could be any combination that allows the material to fit completely within the transformer vessel without contacting any other non-transformer oil components, the vessel or the sealable lid. The holder could attach at any or all edges of the metal sheet as long as the active metal sheet surface's exposure to the sulfur containing component allows for metal sulfide formation/deposition. In one embodiment, the copper metal sheet is replaced with aluminum to target $Al_2S_3$ formation. In one embodiment, the copper metal sheet is replaced with zinc to target ZnS formation. In one embodiment, the metal sheet is rectangular and attached to a holder threaded through a sealable port on a long side. In one embodiment, the rectangular metal sheet is bent to prevent contact with any other non-transformer oil components. However, the rectangular shape of the metal (e.g. copper) sheet is just one non-limiting example, and various other shapes of the metal sheet may be used and still function as intended.

A holder, as used herein refers to a branched end of an elongated structure, wherein the branched end comprises at least two separate surfaces. The surfaces must be cable of exerting continual pressure on an item occupying some or all of an interspace between the branched surfaces. A holder will also possess a mechanism for varying the interspace volume between branched surfaces and the applied pressure to the item. An item to be held is placed within the interspace at any edge or face of the material to be held. The holder's interspace volume is varied until the item is held firmly and securely by holder. Exemplary holders include a three pronged clamp, a C-clamp and a vise grip clamp. However, these are just a few non-limiting examples, and various other holder types may be used and still function as intended.

The present disclosure also relates to an apparatus incorporating a power transformer comprising iron strips (503) and copper windings (408) coated with an insulating dielectric paper (409), wherein the power transformer is held in the vessel with a second holder (310) connected to the second sealable port (204).

As used herein the term "power transformer" refers to iron strips, copper windings, and insulating dielectric tape connected to one another via a holding structure in direct contact with one another. When combined with the sulfur containing transformer oil, the terms "active components of the internal vessel" will apply. The materials for the power transformer could be any chalcogenide active or chalcogenide inactive material based upon the testing parameters desired. One purpose of the power transformer is to model the operation of an industrial transformer in order to find potential corrosion sources due to sulfur containing components. The insulating dielectric paper is envisioned as an electrical insulator around the conductive components of the power transformer. The insulator prevents arcing and short circuiting in transformer operation. In one embodiment the insulating dielectric paper is composed of cellulose. In one embodiment, the insulating dielectric paper is composed of synthetic fibers. The thickness of the insulating dielectric paper, as well as the other active components of the internal vessel could be varied according to the transformer system model parameters desired. In one embodiment, the mass % of the insulating dielectric paper is 1-20%, preferably 2-10%, more preferably 3-5% relative to the total mass of the power transformer. It can be envisioned where the internal active components mass is greater than the transformer vessel and could require an external stabilizing device to secure the system. In one embodiment, the transformer vessel internal active components are attached via cables to a platform wherein the mass of the platform is 100-500%, preferably 200 to 450%, more preferably 300 to 400% of the total mass of the fully assembled apparatus.

The apparatus of the present disclosure also incorporates a weighing device (505) for massing the deposited $Cu_2S$, while still enclosed within the transformer vessel.

It is advantageous that the weighing device is configured to provide a weight readout of the copper metal sheet, the power transformer and the $Cu_2S$ which has deposited onto the reactive surfaces in real time. In one embodiment, a weighing device for measuring the mass/weight of $Cu_2S$ formed on the copper metal sheet is attached to the copper sheet and secured by the first holder. However, one or multiple weighing devices could be attached to the transformer vessel through any sealable port. In one embodiment, the weighing device (505) is attached to the power transformer and secured via the second holder. In one embodiment a first weighing device is attached to the copper sheet and secured via the first holder, and a second weighing device is attached to the power transformer and secured via the second holder. In one embodiment, the weighing device is attached to the copper sheet via the first holder and connected via conductive wires (306) through the third sealable port (205) to an electronic readout mounted to a ground surface. In one embodiment, an electronic readout is wired to the weighing device through the first sealable port, and mounted on top of the sealable lid with an adhesive. It can also be envisioned where a gauge could be used in place of the electronic readout.

The present disclosure also relates to an apparatus incorporating a temperature sensor (308) held in the vessel with a third holder connected to a third sealable port (205).

A temperature sensor is a measuring device composed of two or more dissimilar conductors, where a temperature differential is experienced by the two. A voltage is subsequently produced when a temperature at a point on the thermocouple differs from a reference temperature at other parts of the circuit. As describe herein, a temperature sensor maybe a thermistor, a thermocouple, a resistance thermometer, or a silicon bandgap temperature sensor. The temperature sensor could be wired into a heating source to provide feedback data on the internal temperature of the transformer oil, and permit a looped system where the temperature can be automatically set and maintained. However, the temperature sensor could be envisioned as wired into a stand-alone device. In one embodiment, the thermocouple consists of more than one metallic alloy, a conductive wire linking the alloys to a heating bath temperature controller (309) and a display (305). In one embodiment, the thermocouple provides internal transformer temperature feedback data to a heating bath temperature controller.

The present disclosure also relates to an apparatus incorporating a reactive sulfur-containing insulating transformer oil that submerges, or at least partially submerges, the copper metal sheet, the power transformer, and the temperature sensor. The apparatus of the present disclosure enables measurement of an amount of reactive sulfur species in the sulfur containing insulating transformer oil and a rate of formation of $Cu_2S$ deposits.

"Reactive sulfur" as used herein refers to sulfur species including but not limited to, elemental sulfur, thiols, sulfides, and at elevated temperatures, disulfides and thiophenes. It is also envisioned that reactive selenium, and tellurium analogs present in active components could be found. In one embodiment, a reactive insulating transformer oil containing diphenyl diselenide, a selenium analog of disulfides is used to submerge the components of the apparatus.

"Components", as used herein may include but is not limited to, insulator dielectric tape, transformer gaskets, transformer oil, and copper windings. In one embodiment a transformer O-ring gasket is the reactive sulfur containing component wherein an O-ring gasket is submerged or at least partially submerged in a transformer oil with a known $Cu_2S$ formation rate. As a viable component in industrial power transformers, the contribution of gaskets to the formation of corrosive sulfur species should not be ignored.

The present disclosure also relates to an apparatus incorporating a heating bath that heats the transformer vessel.

A heating bath refers to an apparatus used to increase the internal temperature of the transformer vessel and or the active internal components. In one embodiment a heating mantle with the transformer vessel seated inside of it is used.

The present disclosure also relates to an apparatus incorporating a gas bubbler (401) fluidly connected to a fourth sealable port (206), wherein the gas bubbler is fluidly connected to an inert gas source, and the gas bubbler maintains an inert atmosphere and constant pressure within the transformer vessel.

A "gas bubbler" as used herein refers to a structure or device used to visually or audibly determine if there is an active gas flow through an otherwise closed system. In one embodiment, a gas bubbler is a closed transparent glass vessel, with sealable inlet (404) and outlet (403) ports as well as a single stoppered open necked aperture wherein the open necked aperture is attached at one end to the fourth sealable port of the sealable lid and an elongated hollow glass rod with a small opening at either end extending into the bubbler vessel. The internal cavity of the bubbler may be filled with a liquid material covering at least up to the distal end of the elongated rod. In one embodiment, mercury is used as the liquid material. The liquid/metal material could serve role as an visual/auditory indicator of gas flow. In one embodiment, mercury is the liquid material in a gas bubbler wherein the flow of gas into the liquid induces bubble formation and a rattling noise.

The gas bubbler could also serve the role of restricting external oxygen from entering the transformer vessel, while allowing internal gaseous species to exit via sealable gas ports. For example, incoming oxygen could be unable to displace a more dense bubbler liquid material from around the distal elongated end leading into the transformer vessel. It is envisioned other forms of the gas bubbler may be used in lieu of glass bubblers including but not limited to, oil bubblers, gas regulators, water bubblers and metal bubblers.

"Fluidly connected", as used herein refers to a sealed coupling with no points of exposure to the external environment between the origin and end points of the coupling. In one embodiment, the transformer vessel is connected to the gas bubbler via a singular piece of elongated tubing, wherein the tubing is secured to transformer vessel and the gas bubbler via at least one fastener. In one embodiment, the inert gas source is connected directly to the transformer vessel via a first piece of tubing to the first sealable port, and the gas bubbler is fluidly attached at the fourth sealable port via a second piece of tubing. In one embodiment the inert gas source is connected directly to a gas bubbler, comprising a gas inlet port, a gas outlet port, a sealable gas release valve and a sealable open neck aperture, wherein a first piece of tubing connects the gas bubbler's inlet port and an inert gas source outlet port, and a second piece of tubing connects the gas bubbler outlet port and the transformer vessel's fourth sealable port, and the gas bubbler's release valve allows the removal of gas from the transformer vessel. It is envisioned other configurations and materials may be used, including but not limited to rubber tubing, multiple glass tubing, flex tubing and PVC pipe. Gas flow controllers, and additional sealable inlets could also be envisioned. Gas flow controllers, as used herein, refers to any device or structure used to direct, start, stop or interrupt the propagation of gas through a system. Exemplary gas flow controllers include but are not limited to valves, stopcocks, switches, solenoids and tube clamps. In one embodiment, the tubing has a gas flow controller between that can be used to regulate or stop the flow of gas through the tubing. In one embodiment, the tubing has a gas inlet port that can be used to remove gas from the internal vessel environment. In one embodiment, the gas flow controller is a stopcock that can be used to regulate or stop gas flow through the tubing.

"Inert gas source" as used herein includes but is not limited to, any standing gas supply of nitrogen, or argon. In one embodiment, the inert gas source is a compressed gas tank with a regulator of nitrogen.

The present disclosure also relates to an apparatus incorporating a reactive sulfur-containing insulating transformer oil that submerges at least a portion of the held copper metal sheet, the power transformer, and the temperature sensor. Sulfur-containing insulating transformer oil as used herein includes but is not limited to, mineral oil, coconut oil, polychlorinated biphenyls, fluorinated hydrocarbons, and silicon based hydrocarbons. In one embodiment, the reactive sulfur containing insulating transformer oil has a sulfur species content of 0.0001-50%, preferably 0.0005-45%, more preferably 0.001-40% by weight, relative to the total weight of the sulfur-containing insulating transformer oil. The apparatus of the present disclosure is used to measure reactive sulfur species from the sulfur containing insulating transformer component to determine a rate of $Cu_2S$ deposit formation.

According to a second aspect, the present disclosure relates to a method for measuring reactive sulfur species formation in a power transformer, involving purging the apparatus of the present disclosure, in one or more of its embodiments, with an inert gas.

Purging, refers to replacing the gaseous environment inside of a vessel by introducing a steady gas flow of the desired gas composition from a standing gas source and evacuating the undesired gas from the environment. For reactions where the active components and products are sensitive to oxygen, inert gases are used as the purging gas. As previously discussed the inert gas could include but is not limited to, nitrogen, and/or any noble gas. A confirmation of active gas flow into the vessel is achieved by visually or audibly monitoring a gas bubbler fluidly attached at an inlet port to the inert gas source and attached to the desired vessel at the bubblers outlet port. Evacuating as used herein, refers to a process where the internal gaseous environment is actively or passively removed from the vessel. In the present disclosure the evacuation process could be coupled to the purging process to create a single direction gas flow system.

In one embodiment, nitrogen gas is the inert purging gas, wherein the evacuating process proceeds through a third sealable port on the transformer vessel.

The method also involves heating the apparatus to a reactive temperature with the heating bath (302).

In the present disclosure, "heating", refers to the process of actively raising the internal temperature of the transformer vessel's contents to a set value or range. The release of reactive sulfur containing species from the sulfur containing active components can be initiated by the heating process, wherein a reactive temperature is reached and maintained over a period of time to propagate the formation of $Cu_2S$. The heating process is envisioned to be controlled by a controller apparatus, and measured through a temperature sensor. In one embodiment, the reactive temperature is 30-150° C., preferably 35-130° C., more preferably 40-120° C. In one embodiment, the heating is carried out for up to 30 days, preferably up to 25 days, more preferably up to 20 days. In one embodiment, the internal vessel temperature is measured by a thermocouple.

The method also involves examining the copper metal sheet and the insulating dielectric paper of the power transformer for $Cu_2S$ deposits.

In the present disclosure "examining" refers to a process wherein the presence or absence of the desired product is determined through the review of optical or electronic data. The data could be gathered through a number of methods including but not limited to, direct visual observation, electronic microscopy, X-ray diffraction and computer imaging. In one embodiment, examining the $Cu_2S$ deposit comprises removing the $Cu_2S$ deposit and the power transformer and using at least one characterization method selected from the group consisting of XRD, SEM, and ICP. In one embodiment, the examining is conducted through the transparent transformer vessel and/or the transparent sealable lid, for instance prior to removing.

In the present disclosure, "removing" refers to a process wherein the active internal components are withdrawn from the transformer vessel. This process could be achieved with or without exposure of the internal active components to the external environment. In one embodiment the active internal components are removed by releasing the fastener on the transformer and sealable lid flange and releasing the holders on the active components. In one embodiment, the transformer vessel under an inert environment is placed in a larger inert environment and the active components are removed. It can also be envisioned wherein the removing includes a vacuum process while the transformer vessel remains closed to the external environment.

The method of the present disclosure also involves quantifying the $Cu_2S$ deposits to determine the levels of reactive sulfur species present in the sulfur containing transformer components.

In the present disclosure, "quantifying" refers to a process wherein a numerical value for an observed or recorded phenomena is assigned. In one embodiment the $Cu_2S$ produced is quantified as the difference between the initial mass of the copper metal sheet/power transfer apparatus prior to heating and after heating using a weighing device.

The weighing device as used herein refers to an apparatus attached directly or indirectly to the copper sheet through the first holder and provides real time mass feedback data to a visually accessible gauge or display outside of the internal transformer vessel environment. Since the weighing device could provide real time mass data for the amount of $Cu_sS$ produced, it can be envisioned the quantifying could be completed prior to the removing step. In one embodiment, the initial mass of the copper sheet is observed on the electronic readout prior to heating and recorded, and the final mass is observed and recorded after heating is completed, wherein the entire apparatus is still under an inert gas environment.

"Real-time" as used herein refers to a time scale where the time difference between a change in the data, and the reporting or display of that data change is minimal. In one embodiment, an increase in mass of the copper sheet is exhibited on the electronic display within 10 milliseconds of the event. For example, the copper metal sheet plus any deposits are weighed using the weighing device every 10 ms, The method also includes calculating the rate of formation of $Cu_2S$ deposits.

In the present disclosure "calculating" refers to performing a mathematical operation on a set of dependent values with respect to a set of independent values in order to arrive at a desired quantity. In one embodiment, the calculating comprises plotting the mass of $Cu_2S$ formed at a reactive temperature as function of time of formation. In one embodiment, the calculating further comprises fitting the mass of $Cu_2S$ vs time of formation data to a model and calculating the rate formation.

The invention claimed is:

1. A power transformer monitoring system, comprising:
    a cylindrical transformer vessel with a sealable lid comprising at least four sealable ports, and a flange on both the vessel and the sealable lid, wherein the cylindrical transformer vessel and the sealable lid are glass;
    a copper metal sheet held in the cylindrical transformer vessel with a first holder connected to a first sealable port;
    a power transformer comprising iron strips and copper windings coated with an insulating dielectric paper, wherein the power transformer is held in the cylindrical transformer vessel with a second holder connected to a second sealable port;
    a temperature sensor held in the vessel with a third holder connected to a third sealable port;
    a gas bubbler fluidly connected to a fourth sealable port and an inert gas source, wherein the gas bubbler maintains an inert atmosphere and constant pressure within the cylindrical transformer vessel;
    a heating bath that heats the transformer vessel; and
    a weighing device attached to the first holder for measuring a mass/weight of $Cu_2S$ deposits formed on the copper metal sheet;
    wherein the apparatus enables measurement of an amount of reactive sulfur species in a sulfur containing insulating transformer oil and a rate of formation of the $Cu_2S$ deposits.

2. The power transformer monitoring system of claim 1, wherein the cylindrical transformer vessel further comprises a gasket seated on the flange of the vessel, and when sealed, the gasket is sandwiched between the flange of the cylindrical transformer vessel and the flange of the sealable lid.

3. The power transformer monitoring system of claim 2, wherein the sealable lid is secured to the cylindrical transformer vessel via at least one fastener selected from the group consisting of a clamp, a screw, a bolt, and an adhesive by fastening together the flange of the cylindrical transformer vessel and the sealable lid flange.

4. The power transformer monitoring system of claim 1, wherein the temperature sensor is a thermocouple comprising more than one metallic alloy and a conductive wire.

5. The power transformer monitoring system of claim 4, further comprising a heating bath temperature controller that is electrically connected to the heating bath, the thermocouple, and a display,
 wherein the conductive wire of the thermocouple links the metallic alloys to the heating bath temperature controller.

6. The power transformer monitoring system of claim 5, wherein the thermocouple provides internal transformer temperature feedback data to the heating bath temperature controller.

7. The power transformer monitoring system of claim 1, wherein the insulating dielectric paper comprises cellulose.

8. The power transformer monitoring system of claim 1, wherein the reactive sulfur containing insulating transformer oil comprises at least one reactive sulfur containing species selected from the group consisting of elemental sulfur and thiol.

* * * * *